United States Patent [19]

Wheland

[11] Patent Number: 5,164,475
[45] Date of Patent: Nov. 17, 1992

[54] POROUS SUBSTRATES WITH A HIGH CONCENTRATION OF AMINE GROUPS

[75] Inventor: Robert C. Wheland, Wilmington, Del.

[73] Assignee: Du Pont Merck Pharmaceutical Company, Wilmington, Del.

[21] Appl. No.: 473,071

[22] Filed: Jan. 31, 1990

Related U.S. Application Data

[63] Continuation-in-part of Ser. No. 304,737, Jan. 31, 1989, abandoned.

[51] Int. Cl.⁵ .............................................. C08G 69/26
[52] U.S. Cl. .................................. 528/335; 428/474.4; 521/184; 525/125; 525/126; 525/128; 525/170; 525/432; 528/338
[58] Field of Search ............................. 536/27, 28, 29; 525/125, 126, 128, 170; 435/6, 180; 428/474.4; 528/338, 335; 521/184

[56] References Cited

U.S. PATENT DOCUMENTS

| | | |
|---|---|---|
| 3,743,597 | 7/1973 | Credali et al. ........................ 210/54 |
| 3,876,738 | 4/1975 | Marinaccio et al. .................. 264/41 |
| 4,340,479 | 7/1982 | Pall ..................................... 210/490 |
| 4,450,126 | 5/1984 | Kesting ................................ 264/41 |
| 4,455,370 | 6/1984 | Bartelsman et al. ..................... 435/6 |
| 4,806,546 | 2/1989 | Carrico et al. ......................... 536/27 |

FOREIGN PATENT DOCUMENTS 0343745 11/1989 European Pat. Off. .
1949847 4/1970 Fed. Rep. of Germany .
2197921 3/1974 France .
2247489 5/1975 France .

OTHER PUBLICATIONS

E. M. Southern, J. Molecular Biology, vol. 98, p. 503 (1975).
Bittner et al., Anal. Biochem, vol. 102, p. 459, (1980).

*Primary Examiner*—Johnnie R. Brown
*Assistant Examiner*—James O. Wilson

[57] ABSTRACT

The invention relates to a polyamide substrate with a high concentration of amine groups, and a method of transferring biological materials by adsorption onto said substrate.

8 Claims, No Drawings

POROUS SUBSTRATES WITH A HIGH CONCENTRATION OF AMINE GROUPS

CROSS-REFERENCE TO RELATED APPLICATIONS

This is a continuation-in-part of copending patent application Ser. No. 07/304,737, filed on Jan. 31, 1989; now abandoned.

FIELD OF THE INVENTION

This invention relates to porous substrates with a high concentration of amine groups and to the use of such substrates to transfer and immobilize nucleic acids, proteins, bacteria, and viruses from electrophoresis gels or culture media to a substrate.

BACKGROUND OF THE INVENTION

A number of materials and methods have been developed for transferring substances from a gel or culture medium to an immobilizing membrane.

E. M. Southern (J. Molecular Biology, Vol. 98, p. 503, 1975) has disclosed a method for transferring nucleic acids from electrophoresis gels to an adsorptive medium. In the Southern method, the membrane is placed between the gel and a few layers of paper towels. As buffer solution is forced through the gel and membrane and into the paper towels by capillary action, the nucleic acid sample is driven into and deposited on the membrane. This is referred to as transfer by blotting.

Bittner et al. (Anal. Biochem., Vol. 102, p. 459, 1980) disclosed a similar method in which an electrical potential is used drive the nucleic acid sample into the membrane. This is referred to as electrophoresis transfer or electroblotting.

Adsorptive microporous membranes have also been used to transfer bacteria and viruses from growth media.

Several materials have been effectively used for use as transfer membranes, including nitrocellulose, nitrobenzyloxymethyl cellulose, aminobenzyloxymethyl cellulose, aminophenyl-thioether cellulose, diethylaminoethyl cellulose, and polyvinylidene fluoride. The cellulose-based materials are however brittle and frequently break up during the transfer process or the manipulations involved in subsequent analytical procedures.

U.S. Pat. No. 4,455,370 broadly discloses the use of microporous adsorptive nylon films as transfer films.

Methods for plasma-etching polyolefins in the presence of ammonia are, of course, known in the art.

U.S. Pat. No. 4,340,479 discloses a process for preparing skinless hydrophilic alcohol-insoluble polyamide membranes comprising preparing a solution of an alcohol-insoluble polyamide resin in a polyamide resin solvent, inducing nucleation of the solution by controlled addition of a nonsolvent for the polyamide resin to the polyamide resin solution to obtain a visible precipitate of polyamide resin particles, thereby forming a casting solution; spreading the casting solution on a substrate to form a film on the substrate, contacting and diluting the film of casting solution with a nonsolvent for the polyamide resin, thereby forming a membrane, washing the membrane to remove solvent, and drying the resulting membrane. The reference teaches that although the starting polymers are available in a wide variety of grades, which vary appreciably with respect to molecular weight and in other characteristics, the formation of a hydrophilic membrane appears to be a function not of these characteristics, but of the chemical composition of the polymer.

U.S. Pat. No. 3,876,738 discloses a process for the production of microporous films by casting or extruding a solution of a film-forming polymer in a solvent system into a quenching bath which is comprised of a nonsolvent system for the polymer. The polymers employed are preferably nylon polymers. There is no discussion of advantages which might accrue to the use of various molecular weight grades of nylon.

SUMMARY OF THE INVENTION

This invention represents an improvement over other membranes. This invention relates to a composition of matter, a polyamide substrate which has a high surface concentration of amine groups optionally supported by an inert support.

This invention also relates to an improved method for the transfer of materials such as nucleic acids, proteins, bacteria, or viruses preferably from gel a or culture to a porous substrate, wherein the improvement comprises contacting the material with a polyamide substrate which has a high concentration of amine groups.

This invention relates further to the transfer of nucleic acids or proteins from an electrophoresis gel to a polyamide substrate with a high concentration of amine ends by blotting or electroblotting. It also relates to transfer of nucleic acids, proteins, bacteria, or viruses from culture media (including plaques) by contacting the substance to be transferred in the medium with a polyamide substrate which has a high surface concentration of amine groups.

DETAILED DESCRIPTION OF THE INVENTION

This invention relates to a porous substrate which has a high surface concentration of amine groups.

It is critical that the polyamide substrate have a high surface concentration of amine groups in order to bind nucleic acids or other biological materials. Preferably, the concentration of amine groups should be at least about 60 equivalents per $10^6$ grams. Preferably, the surface area of the substrate should be at least about 1 $m^2/g$, as measured by nitrogen adsorption.

Suitable amine groups are characterized as —NRR', where R and R' are independently H, $C_{1-10}$ branched, unbranched or cylic alkyl or $C_{7-12}$ aralkyl, where the alkyl, aryl or aralkyl groups may contain heteroatom substituents such as halogens or ether oxygens which do not interfere with binding of the biological samples to the porous substrate.

Pore size of the substrates is expressed in terms of bacterial filtration ratings. For example, ability to quantitatively remove the organism *Pseudomonas diminuta* is accepted as defining a 0.2$\mu$ bacterial rated filter, and ability to quantitatively remove the organism *Serratia marcescens* is acepted as defining a 0.45$\mu$ bacterial rated filters. Materials with bacterial filtration ratings in the range of about 0.2$\mu$ to 0.8$\mu$ are preferred, although materials with larger or smaller ratings can be used. For transfer of DNA molecules smaller than about 1 kB and for RNA, the 0.2$\mu$ rated materials are preferred. For transfer of DNA molecules larger than about 1 kB, the 0.45–0.8$\mu$ materials are preferred. In contrast, pore size does not seem to be as important in the transfer and retention of protein molecules, bacteria, or viruses.

The polyamide substrate of this invention may be a homogeneous material, such as a polymeric film or membrane fabricated by techniques known in the art from polymers, or mixtures of polymers, which contain a high concentration of amine groups.

A preferred substrate is a blend of low molecular weight polyamides (for high amine group concentration) and high molecular weight polyamides (for strength). Most preferably, the blend comprises about 1 to 90% by weight low molecular weight polyamide and about 10 to 99% by weight high molecular weight polyamide. Higher percentages of low MW material usually result in brittle blends. The concentration of amines in the low MW polyamides should be $\geq 70$ amine equivalents/$10^6$ g (i.e., 70 moles of amine groups per $10^6$ g of polyamide) to impart a high surface concentration of amine groups to the substrate, but $<1,500$ amine equiv./$10^6$ g to maintain water-insolubility of the amine-rich portion of the polymer blend. The concentration of amine in the high MW polyamides is $<60$ amine equivalents/$10^6$ g. It will be appreciated by those skilled in the art that a compromise is necessary between the desire to have a substrate with a high surface concentration of amine groups and the necessity of incorporating a sufficient amount of high MW material to maintain structural integrity of the substrate. It may not, therefore, be possible to make a suitable substrate by using a large amount of high amine equivalent, low molecular weight polyamide. It has been found that for beneficial DNA adsorption, the final membrane has at least 60 amine ends/$10^6$ g of polymer.

Blends of other low molecular weight, amine-ended or in chain amine polymers with compatible high molecular weight polymers should also give porous substrates with high surface concentrations of amine groups.

High surface concentrations of amine groups can also be achieved by coating or impregnating an inert support with a polymer or mixture of polymers which contain a high concentration of amines. Suitable inert supports include, but are not limited to, cellulose, polyolefins, polyamides, polyesters, and fiberglass.

The effectiveness of the substrate for transferring nucleic acids and other biological materials can be tested by procedures disclosed in U.S. Pat. No. 4,455,370, which procedures are herein incorporated by references.

In preparing compositions according to the invention, it is preferable to use 0.074 ml methanol per ml of formic acid casting solution. Although methanol may not be necessary, its addition to the casting solution brings the polymer to the point of precipitation. Methanol is preferably used in the quench bath as a 1:1 solution of methanol:water or any other nonsolvent or nonsolvent mixture giving a microporous structure. Glass is the preferred casting substrate, although any inert smooth surface allowing spreading of casting dope and easy release of membrane may be used. The compositions are preferably prepared at ambient temperature.

EXAMPLES

Comparative Example 1

Membrane Preparation

High amine 66 nylon membrane cannot be made by the methods disclosed in U.S. Pat. No. 3,876,738.

A 66 nylon sample was obtained with 80 equivalents of amine/$10^6$ g of polymer by means known in the art. A 16 g sample of the nylon was dissolved at ambient conditions in 63 ml of 96% formic acid and 9.0 ml of methanol. This solution was cast on glass as a 10 mil thick film and then quenched for 10 minutes in 1000 ml of either 1:3 or 3:1 methanol:water. The film, still on the glass support, was removed from the bath and air dried. The film was too weak to be removed as a single piece either dry or after rewetting with water.

A glass plate was sprayed with Teflon ® Dry Lubricant before casting. The final films no longer adhered to the glass, but shrank and cracked to useless fragments on drying.

Apparently, nylon samples with high concentrations of amine ends are too low in molecular weight to give porous substrates with adequate strength.

EXAMPLE 1

Low Adsorption with Low Ends, Plain Membrane

A 66 nylon sample (Zytel TM 42) was obtained with 20 equivalents of amine and 44 equivalents of carboxyl/$10^6$ g of polymer. A 72 g sample of this nylon was dissolved in 190 ml of formic acid. Then 14 ml of methyl alcohol were added and the solution tumbled again to homogeneity. This solution was cast 10 mil thick on glass, plunged 30 seconds later in 1000 ml of 1:1 methanol:water, removed and drained after 3 minutes, air dried, stripped from the glass while wet with water, and dried again. In DNA adsorption experiments (in which a scintillation counter is used to quantify the adsorption of radioactive probe) this membrane averaged 1894 disintegrations per minute (DPM). A duplicate membrane analysed for 24 amines/$10^6$ g of polymer.

EXAMPLE 2

Low Adsorption with Low Ends, Membrane on Reemay TM

A 66 nylon sample (Zytel TM 42) was obtained with 20 equivalents of amine and 44 equivalents of carboxyl/$10^6$g of polymer. A 72 g sample of this nylon was dissolved in 190 ml of formic acid. Then 14 ml of methyl alcohol were added and the solution tumbled again to homogeneity. This solution was cast 10 mil thick on a Reemay TM sheet mounted on a glass plate, plunged 30 seconds later in 1000 ml of 1:1 methanol:water, removed and drained after 3 minutes, air dried, stripped from the glass while wet with water, and dried again. In DNA adsorption experiments this membrane averaged 2547 disintegrations per minute (DPM).

EXAMPLE 3

Intermediate Adsorption with Moderate Ends, Plain Membrane

A 66 nylon sample (Zytel TM 42) was obtained with 20 equivalents of amine and 44 equivalents of carboxyl/$10^6$ g of polymer. Adipic acid was polymerized only to oligomer with hexamethylene diamine affording low molecular weight nylon with $<10$ equivalents of carboxyl and 1170 equivalents of amine /$10^6$ g of polymer. Casting solution was prepared by dissolving 65 g of high molecular weight nylon, 7 g of oligomer, and later 14 ml of methyl alcohol in 190 ml of formic acid. This solution was cast 10 mil thick on glass, plunged 30 seconds later in 1000 ml of 1:1 methanol:water, removed and drained after 3 minutes, air dried, stripped from the glass while wet with water, and dried again. In DNA adsorption experiments this membrane averaged 3015 disintegrations per minute (DPM). A duplicate membrane analysed for 90 amines/$10^6$ g of polymer.

EXAMPLE 4

Intermediate Adsorption with Moderate Ends, Membrane on Reemay ™

A 66 nylon sample (Zytel ™ 42) was obtained with 20 equivalents of amine and 44 equivalents of carboxyl/$10^6$ g of polymer. Adipic acid was polymerized only to oligomer with hexamethylene diamine affording low molecular weight nylon with <10 equivalents of carboxyl and 1170 equivalents of amine /$10^6$ g of polymer. Casting solution was prepared by dissolving 65 g of high molecular weight nylon, 7 g of oligomer, and later 14 ml of methyl alcohol in 190 ml of formic acid. This solution was cast 10 mil thick on a Reemay ™ sheet spread on glass, plunged 30 seconds later in 1000 ml of 1:1 methanol:water, removed and drained after 3 minutes, air dried, stripped from the glass while wet with water, and dried again. In DNA adsorption experiments this membrane averaged 3520 disintegrations per minute (DPM).

EXAMPLE 5

High Adsorption with High Ends, Plain Membrane

A 66 nylon sample (Zytel ™ 42) was obtained with 20 equivalents of amine and 44 equivalents of carboxyl/$10^6$ g of polymer. Adipic acid was polymerized only to oligomer with hexamethylene diamine affording low molecular weight nylon with <10 equivalents of carboxyl and 1170 equivalents of amine /$10^6$ g of polymer. Casting solution was prepared by dissolving 58 g of high molecular weight nylon, 14 g of oligomer, and later 14 ml of methyl alcohol in 190 ml of formic acid. This solution was cast 10 mil thick on glass, plunged 30 seconds later in 1000 ml of 1:1 methanol:water, removed and drained after 3 minutes, air dried, stripped from the glass while wet with water, and dried again. In DNA adsorption experiments this membrane averaged 3548 disintegrations per minute (DPM). A duplicate membrane analysed for 180 ends/$10^6$ g of polymer.

EXAMPLE 6

High Adsorption with High Ends, Membrane on Remay

A 66 nylon sample (Zytel ™ 42) was obtained with 20 equivalents of amine and 44 equivalents of carboxyl/$10^6$ g of polymer. Adipic acid was polymerized only to oligomer with hexamethylene diamine affording low molecular weight nylon with <10 equivalents of carboxyl and 1170 equivalents of amine /$10^6$ g of polymer. Casting solution was prepared by dissolving 58 g of high molecular weight nylon, 14 g of oligomer, and later 14 ml of methyl alcohol in 190 ml of formic acid. This solution was cast 10 mil thick on a Remay ™ sheet spread on glass, plunged 30 seconds later in 1000 ml of 1:1 methanol:water, removed and drained after 3 minutes, air dried, stripped from the glass while wet with water, and dried again. In DNA adsorption experiments this membrane averaged 5129 disintegrations per minute (DPM).

I claim:

1. A composition of matter comprising a polyamide substrate with a high concentration of amine groups wherein the concentration of amine groups is at least 60 equivalents per $10^6$ grams of polymer.

2. The composition of claim 1 wherein the polyamide substrate is supported on an inert support.

3. The composition of claim 1 wherein the surface area of the substrate is at least about 1 $m^2$/g as measured by nitrogen adsorption.

4. The composition of claim 1 wherein the amine groups are characterized as NRR' where R and R' are independently H, $C_{1-10}$ branched, unbranched or cyclic alkyl or $C_{7-12}$ aralkyl, where the alkyl, aryl or aralkyl groups may contain heteroatom substituents selected from the group consisting of halogens or ether oxygens.

5. A composition of matter comprising a polyamide substrate which is a blend of from about 1 to about 90 weight percent of low molecular weight polyamides containing from about 70 to 1500 amine equivalents per $10^6$ grams of polymer and from about 10 to about 99 weight percent of high molecular weight polyamides containing less than about 6 amine equivalents per $10^6$ grams of polymer; wherein the final concentration of amine groups in the blend is at least 60 equivalents per $10^6$ grams of polymer.

6. The composition of claim 5 wherein the substrate is supported on an inert support.

7. The composition of claim 5 wherein the surface area of the substrate is at least about 1 $m^2$/g as measured by nitrogen absorption.

8. The composition of claim 5 wherein the amine groups are characterized as NRR' where R and R' are independently H, $C_{1-10}$ branched, unbranched or cylic alkyl or $C_{7-12}$ aralkyl, where the alkyl, aryl or aralkyl groups may contain heteroatom substituents selected from the group consisting of halogen or ether oxygens.

* * * * *